(12) United States Patent
Scorsone et al.

(10) Patent No.: US 8,801,942 B2
(45) Date of Patent: Aug. 12, 2014

(54) METHOD FOR MANUFACTURING A FLEXIBLE INTRAOCULAR RETINAL IMPLANT HAVING DOPED DIAMOND ELECTRODES

(75) Inventors: Emmanuel Scorsone, Magny-les-Hameaux (FR); Philippe Bergonzo, Massy (FR); Mathias Bonnauron, Gif sur Yvette Cedex (FR); Michel Bonnauron, legal representative, Avignon (FR); Christine Alice Regine Helene Terrades, legal representative, Avignon (FR); Serge Anne Daniel Bonnauron, legal representative, Avignon (FR); Lucas Claude Jean Francois Bonnauron, legal representative, Avignon (FR); Tanguy Richard Yves Bonnauron, legal representative, Avignon (FR); Gaelle Lissorgues, Le Perreux sur Marne (FR); Lionel Rousseau, Le Perreux sur Marne (FR)

(73) Assignees: Commissariat a l'energie atomique et aux energies alternatives, Paris (FR); Chambre de Commerce et d'Industrie de Paris (ESIEE Paris), Noisy le Grand (FR)

( * ) Notice: Subject to any disclaimer, the term of this patent is extended or adjusted under 35 U.S.C. 154(b) by 49 days.

(21) Appl. No.: 13/703,062

(22) PCT Filed: Jun. 8, 2011

(86) PCT No.: PCT/EP2011/059510
§ 371 (c)(1),
(2), (4) Date: May 9, 2013

(87) PCT Pub. No.: WO2011/154455
PCT Pub. Date: Dec. 15, 2011

(65) Prior Publication Data
US 2013/0228547 A1  Sep. 5, 2013

(30) Foreign Application Priority Data
Jun. 9, 2010  (FR) ...................................... 10 54550

(51) Int. Cl.
*H01L 21/64* (2006.01)
(52) U.S. Cl.
USPC ............................. 216/13; 264/105; 623/6.63
(58) Field of Classification Search
None
See application file for complete search history.

(56) References Cited

U.S. PATENT DOCUMENTS

| | | | | |
|---|---|---|---|---|
| 5,178,957 | A * | 1/1993 | Kolpe et al. | 428/458 |
| 7,960,695 | B1 * | 6/2011 | Kley | 250/306 |
| 8,241,474 | B2 * | 8/2012 | Jiang et al. | 204/433 |
| 8,491,765 | B2 * | 7/2013 | Pickles et al. | 204/400 |
| 2006/0175953 | A1 | 8/2006 | Swain et al. | |
| 2007/0123963 | A1 * | 5/2007 | Krulevitch | 607/115 |
| 2007/0158100 | A1 * | 7/2007 | Greenberg et al. | 174/254 |
| 2009/0258255 | A1 | 10/2009 | Terashima et al. | |
| 2010/0148345 | A1 * | 6/2010 | Eckhardt et al. | 257/690 |
| 2011/0108433 | A1 | 5/2011 | De Sanoit et al. | |
| 2011/0156057 | A1 | 6/2011 | Mazellier et al. | |
| 2011/0184269 | A1 * | 7/2011 | Sauter-Starace et al. | 600/378 |
| 2011/0237921 | A1 * | 9/2011 | Askin et al. | 600/377 |
| 2012/0312353 | A1 * | 12/2012 | Kusterer et al. | 136/249 |
| 2013/0309809 | A1 * | 11/2013 | Eckhardt et al. | 438/107 |
| 2013/0338746 | A1 * | 12/2013 | Guvanasen et al. | 607/116 |

FOREIGN PATENT DOCUMENTS

| | | |
|---|---|---|
| EP | 1 947 220 | 7/2008 |
| FR | 2 917 229 | 12/2008 |
| WO | 2010 012739 | 2/2010 |

OTHER PUBLICATIONS

Hungar, K., et al., Production processes for a flexible retina implant (Eurosensors XVIII, Session C6.6), Sensors and Actuators A Physical, vol. 123-124, pp. 172 to 178, (2005).

Bergonzo, P., "Des Diamants pour la vue," CEA Techno, No. 89, p. 6, (Jun. 2008).

International Search Report Issued Aug. 22, 2011 in PCT/EP11/059510 Filed Jun. 8, 2011.

\* cited by examiner

*Primary Examiner* — Allan Olsen
(74) *Attorney, Agent, or Firm* — Oblon, Spivak, McClelland, Maier & Neustadt, L.L.P.

(57) ABSTRACT

A method for manufacturing an intraocular retinal implant including: providing a mold capable of supporting growth of a layer of doped diamond, the mold including, on one face, elements all depressed or all projecting with respect to the surface of the face, and constituting a pattern cavity for the electrodes of the implant which it is desired to obtain; producing the doped diamond electrodes by growing a layer of doped diamond in all or part of a space occupied by the pattern cavity elements; forming a first insulating layer on the face of the mold including the pattern cavity; producing interconnection lines by depositing an electrically conductive material at least in spaces not covered by the first insulating layer; forming a second insulating layer on the mold face including the pattern cavity, the second layer covering the interconnection lines, the first and second insulating layers forming a flexible plate of the implant; removing the mold.

10 Claims, 8 Drawing Sheets

METHOD FOR MANUFACTURING A FLEXIBLE INTRAOCULAR RETINAL IMPLANT HAVING DOPED DIAMOND ELECTRODES

TECHNICAL FIELD

The present invention relates to the field of implants, the function of which is to restore the vision of patients made blind by a degenerative disease of the retina.

The invention more particularly relates to a method for manufacturing a flexible retinal implant intended to be implanted in the eyeball of a patient and the function of which is to receive and process external visual stimuli that are used to excite the diseased retina of the patient via electrodes.

It is pointed out that the method according to the invention may be applied indiscriminately to the production of "epi-retinal" implants, in other words intended to be arranged on the retina of the patient, or to the production of "sub-retinal" implants, in other words intended to be placed behind the retina.

PRIOR ART

Today, retinal degeneration pathologies, such as for example age related macular degeneration (ARMD), affect around 12 million people in the United States and in Europe. Certain studies have even predicted the growth of this phenomenon on account of the ageing of western populations: according to forecasts, in 2012, 1% of the population will be affected by a retinal pathology at the age of 55 years, 10% at 65, 25% at 75 and up to 60% at 90 years.

Among the most frequent retinal pathologies, retinitis pigmentosa and ARMD lead to a progressive degeneration of photoreceptors, leading to the progressive loss of localised vision on the retina, even though the whole of the neuronal system of the retinal layers is still intact and capable of transporting electrical information to the brain.

In order to restore vision to persons affected by said degenerative diseases of the retina, it is known to implant on the retina retinal prostheses that directly electrically stimulate the still healthy layers of the retinal tissue.

In this respect, the prior art today reports highly varied implant geometries, the common structure of which is formed of a set of electrodes of micrometric size (in other words comprised between 1 and 1000 µm), also known as "microelectrodes", the base of which is arranged on a support substrate made of electrically insulating material, said electrodes being made of an electrically conductive material.

Certain of said implants are composed of metal electrodes arranged on a rigid substrate, for example silicon (see the document [1] referenced at the end of the description). Yet, these types of implants have a certain number of drawbacks. Firstly, their rigidity can damage the retinal tissues during their implantation on or under the retina. In certain cases, the electrode may moreover be brittle. In addition, the lack of flexibility of said implants does not make it possible to obtain a suitable positioning of the implants and in particular to hug correctly the surface of the tissues to be stimulated, which can potentially prevent certain electrodes from coming into contact with the areas of interest to stimulate.

To resolve this problem of rigidity, implants comprising microelectrodes arranged on flexible substrates have been developed. The flexible substrates of said implants are generally manufactured from polyimide or pyralene type polymers, which are materials particularly interesting for their flexibility, as well as for their chemical inertia and their biocompatibility (see the document [2]).

The materials used for the electrodes of the implants are, for their part, generally metals or metal oxides, such as gold, platinum or iridium oxide. Yet, one of the drawbacks of electrodes manufactured on the basis of said materials is that they suffer from corrosion and from a lack of mechanical and chemical stability, in particular in in-vivo medium, which is a relatively hostile medium for metal electrodes. Furthermore, this phenomenon of ageing of the electrodes is accelerated by the passage of a current through the electrodes when they are used for the stimulation. In fact, the use of metal electrodes in the implants imposes the application of high levels of stimulation currents, which induces, in the long term, a premature ageing of the electrodes and requires a ponderous surgical intervention in order to replace the worn out implant.

Furthermore, it is advantageous to have a high density of electrodes on the implant to re-establish the best possible visual acuity. To do this, the size of each electrode must be as small as possible and the electrodes need to be brought together as close as possible, which poses a certain number of problems.

Firstly, the reduction in the size of the electrodes leads to a loss of the capacitance thereof. To resolve this problem, it is necessary to structure the surface of the electrodes in order to increase the specific surface thereof, which is very difficult to achieve on metal electrodes. A possible solution to this problem is to produce the metal electrodes with platinum black, in other words with a stack of platinum particles of nanometric sizes. However, the mechanical strength of this type of electrode is very poor, in particular when they are in contact with living tissues.

Secondly, bringing the electrodes closer together can cause interferences between adjacent electrodes and thereby lead to a loss of resolution of the implant. One way of reducing said potential interferences is to apply less current to the electrodes. However, by reducing the current, the electrodes may then only efficiently stimulate the neuronal cells provided that said cells are as close as possible to the electrodes, or even in direct contact with them. To do this, the electrodes must be constituted of a biocompatible material. A biocompatible material is a material that does not cause necrosis of the surrounding tissues and which has moreover a large affinity with the cells to be stimulated, in other words which is favourable to the coupling of neuronal cells directly on its surface. It is known for example that, in the case of retinal implants, when metal electrodes are used, there is formation of a layer of glial cells that insert themselves between the surface of the electrode and the neuronal tissues, which affect electrical transmission between the neurones and the electrode.

In this context, those skilled in the art have thus sought alternative materials to metal materials, having a better stability and a better affinity with living tissues. It is in this way that electrodes have been proposed based on nanotubes of carbon, which potentially has a better stability and a better affinity with living tissues than metal electrodes. However, electrodes based on nanotubes are very fragile and have a tendency to break on contact with the biological tissues and become uncoupled, through friction, from the support substrate on which they are arranged.

The inventors have, for their part, proposed producing implants based on electrodes made of doped diamond arranged on a flexible substrate made of biocompatible and electrically insulating material such as polyimide (document [3]). In fact, since diamond is constituted of carbon, it has a much better biocompatibility than any metal. Also, by creating electrodes made of doped diamond, it may be hoped to limit the body's defence reactions vis-à-vis the implant (such as, for example, glial reactions), thereby obtaining a better contact between the living tissues and the implant by favouring the absence of rejection of the implant. By improving the biocompatibility, it may also be hoped to reduce the stimulation currents and thereby increase the number of pixels and, ultimately, improve the definition of the image recreated thanks to the implant.

However, the growth of the diamond is generally carried out in a CVD (Chemical Vapour Deposition) reactor by a micro-wave or radiofrequency or hot filament plasma enhanced diamond growth technique, well known to experts in the field of the growth of synthetic diamond. The growth of the diamond is thus obtained by chemical vapour deposition in a plasma in the presence of hydrogen and a source of carbon, for example methane. The deposition is thus carried out at a temperature comprised typically between 500 and 1000° C. Yet, said temperature scale is incompatible with the growth of synthetic diamond on the flexible substrates made of polymers commonly used for the production of flexible implants. The production of said implants thus seems compromised. The inventors have thus set themselves the aim of elaborating a method making it possible to produce said implants with flexible substrates and with electrodes made of doped diamond.

DESCRIPTION OF THE INVENTION

The subject matter of the invention is thus a method for manufacturing an intraocular retinal implant, intended to stimulate cells of the retina by sending electrical impulses to produce an artificial vision, said implant including a flexible plate made of a biocompatible and electrically insulating material, which is provided, on one of the face thereof, with a plurality of electrodes made of doped diamond spaced apart from each other and connected to interconnection lines intended to lead an electric current to the electrodes so that they can transmit electrical impulses to said cells of the retina, said method including the following successive steps:

providing a mould capable of supporting the growth of a layer of doped diamond, said mould comprising, on one of the face thereof, a set of elements which are all depressed or all projecting with respect to the surface of said face, and which constitute a pattern cavity for the electrodes of the implant which it is desired to obtain;
  producing electrodes made of doped diamond by growing a layer of doped diamond in all or part of the space occupied by the elements of the pattern cavity;
  forming a first layer of electrically insulating material on the face of the mould comprising the pattern cavity, said first layer covering at least the space between the electrodes, while leaving uncovered at least a part of the surface of each electrode;
  producing interconnection lines by depositing an electrically conductive material at least in the spaces not covered by the first layer of electrically insulating material;
  forming a second layer of electrically insulating material on the face of the mould including the pattern cavity, said second layer covering the interconnection lines and the first and the second layers of electrically insulating material forming the flexible plate of the implant; and
  removing the mould.

By proceeding in this manner, the electrodes of the implant are projecting (in other words in relief) with respect to the face on which they are arranged.

It should be noted that the plate of the implant is flexible, which implies that the thickness of the first and the second layers of electrically insulating material is less, for determined materials, than a threshold value that those skilled in the art are capable of determining. It is pointed out that a flexible plate is a plate that is flexible, in other words which has a bending deformation greater than or equal to a determined limit value when the determined pressure is applied on the surface of said layer.

The flexible substrate is preferably a polymer selected for its appropriate mechanical properties, as well as for its biocompatibility and its biostability. Said polymer will be for example a siliconised polymer, a polyimide or a pyralene.

Advantageously, the materials of the first and the second layer are made of a same material.

Advantageously, removing the mould is obtained by chemical or mechanical elimination of the mould. The elimination may, for example, consist in dissolution in a suitable acid or mechanical sanding. The mould may also be detached by disbondment. For example, the mould may be a substrate made of silicon or glass, because said materials may be dissolved in a suitable mixture of nitric and hydrofluoric acids for the first, or in hydrofluoric acid alone, for the second.

According to a variant, the method moreover includes, between the step of providing a mould and the step of producing the electrodes, a step of depositing, on the face of the mould comprising the pattern cavity, a sacrificial layer supporting the growth of a layer of doped diamond, said sacrificial layer being intended to be removed during the step of removing the mould. Said sacrificial layer then has the function of facilitating removing the mould. In this case, removing the mould is advantageously obtained by dissolution of the sacrificial layer or by detaching the sacrificial layer. The detachment of the sacrificial layer is possible when the material of the sacrificial layer is selected such that it has an adhesion coefficient on the doped diamond and on the first layer of electrically insulating material which is less than the adhesion coefficient of the sacrificial layer on the mould. As for the dissolution of the sacrificial layer, it may be obtained by using a suitable solvent (acid, etc.). For example, it is possible to deposit a silicon oxide layer on a silicon substrate; the oxide layer will be etched at the end of the method in a hydrofluoric acid solution. Alternatively, the sacrificial layer may also be a metal layer that will be dissolved by electro-erosion.

It is pointed out that, since the sacrificial layer is intended to be removed, it suffices that it supports the growth of the doped diamond and may equally well be made of an electrically insulating or conductive material.

Advantageously, the electrodes have an elongated shape with a height that is at least two times greater than the base, the base being the part of the electrode in contact with the layer of first electrically insulating material. The electrodes may thus be elements of column, needle or point shape. Advantageously, the height of the electrodes is calculated such that the end of the electrodes can reach the retinal cells that it is wished to stimulate.

Preferably, the electrodes are arranged perpendicularly to the surface of the flexible plate.

The cells of the retina that it is possible to stimulate using electrodes may be ganglions, bipolar cells, neurons, etc.

Advantageously, the electrodes are arranged according to a pattern that reflects the lay out of the cells of the retina that it is wished to stimulate.

Advantageously, the electrodes form an array. Preferably, said array has a regular pitch.

Advantageously, the largest extent of the electrodes measured in a direction parallel to the plane of the face of the flexible plate comprising the electrodes is of micrometric dimension or less. Said extent is, preferably, nanometric, in other words comprised between 1 and 1000 nm.

Advantageously, the distance that separates two adjacent electrodes is of micrometric dimension or less. Preferably, said distance is nanometric.

The doping of the diamond makes it possible to render the material electrically conductive, in order to be able to use it to convey the electrical signals that will serve for the cell stimulation. The diamond may be doped with any material and in sufficient quantities to make the doped diamond electrically conductive. Preferably, the doped diamond is diamond doped with boron. It is in fact known that diamond doped with boron has excellent electrochemical, biocompatibility and mechanical stability properties, which makes it an ideal material for producing the electrodes of our implant. Preferably, the boron concentration in the doped diamond is comprised between $10^{18}$ and $10^{21}$ atoms per $cm^3$.

The provision of the mould may be obtained in different ways.

According to a first variant, the provision of the mould includes the following successive steps:
providing a substrate capable of supporting the growth of a layer of doped diamond on one of the faces thereof;
depositing a layer of diamond powder on said face of the substrate, the grains of the diamond powder having a nanometric size;
depositing a layer of photosensitive resin of a determined thickness on the layer of diamond powder;
structuring the layer of diamond powder by photolithography of the layer of photosensitive resin to obtain the pattern cavity of the mould.

According to a second variant, the provision of the mould includes the following successive steps:
providing a substrate capable of supporting the growth of a layer of doped diamond on one of the faces thereof;
depositing a layer of diamond powder on said face of the substrate, the grains of the diamond powder having a nanometric size;
depositing a layer of photosensitive resin of a determined thickness on the layer of diamond powder;
structuring the layer of photosensitive resin by photolithography until the layer of diamond powder is reached;
depositing a metal layer on the face of the substrate, said metal layer covering the structured resin layer and the layer of diamond powder not masked by the structured resin layer;
removing the structured resin layer so as to form a structured metal layer;
structuring the layer of diamond powder by etching the layer of diamond powder not masked by the structured metal layer;
removing the structured metal layer to obtain the pattern cavity of the mould. A substrate is thereby obtained comprising a structured layer made of diamond nanopowders.

The formation of the structured metal layer may be obtained by a lift-off method.

The structuring of the layer of diamond powder may be carried out by plasma etching of the layer of diamond powder not protected by the structured metal layer.

According to a third variant, the mould is obtained by locally etching the face of a substrate capable of supporting the growth of a layer of doped diamond so as to form a mould having the inverse geometry to that of the desired electrodes, in other words, forming the negative pattern cavity of the electrodes. To carry out the structuring of the face of the substrate and thereby produce the mould, all means of liquid or dry etching known to those skilled in the art may be used. As regards the choice of materials capable of supporting the growth of the doped diamond, it is preferable to select materials that may easily be etched, such as silicon or glass. In a silicon substrate, the cavities may be produced by known techniques of localised etching such as RIE ("Reactive Ion Etching") or DRIE ("Deep Reactive Ion Etching"). Etchings in liquid solutions may also be carried out, in hydrofluoric acid based solutions, for glass, or in potassium hydroxide (KOH) based solutions, for silicon.

The growth of the synthetic doped diamond is, for its part, obtained by a CVD (Chemical Vapour Deposition) growth method: the growth of the doped diamond is carried out in a micro-wave or radiofrequency or hot filament plasma enhanced CVD growth reactor, a technique well known to experts in the field of the growth of synthetic diamond. The growth is carried out by chemical vapour deposition in a plasma in the presence of hydrogen, a source of carbon, for example methane, and a source of dopant. In the case of the growth of diamond doped with boron, the source of boron is for example trimethyl boron ($B(CH_3)_3$) or diborane ($B_2H_6$). The deposition is carried out at a temperature comprised typically between 500 and 1000° C.

Obviously, in order to initiate the growth of a film of doped diamond, diamond particles of nanometric sizes (preferably, a size comprised between 5 and 100 nm) are arranged at the locations where it is wished to obtain electrodes, in other words on the whole of the upper face of the substrate to form a continuous film in the case where the mould is obtained by structuring a layer of diamond powder, or localised on the walls of the cavities of the mould, in the case where the mould is already structured. The diamond particles are laid out according to a density typically comprised between $10^8$ and $10^{11}$ particles per centimeter squared, using techniques well known to those skilled in the art of the growth of diamond, such as for example nucleation enhanced by polarisation or by soaking in a colloidal solution of diamond particles of nanometric size. The growth of said diamond grains by a CVD technique will lead to obtaining a film of polycrystalline diamond.

The interconnection lines make it possible to obtain a setting of contacts between the electrodes made of doped diamond and the electronic instrumentation supplying the energy. Said interconnection lines are tracks made of electrically conductive material deposited locally on the electrodes and the layer made of a first electrically insulating material, then encapsulated, wherever necessary, in a layer of electrically insulating material, which is preferably the same electrically insulating material as that used for the first layer of electrically insulating material. The electrically conductive material is preferably selected from platinum, gold, titanium or any other metal capable of providing an electrical contact of good quality between the electrode and the instrumentation, without degrading over time. Although said metals are encapsulated, it is preferable to select metals that are biocompatible. The deposition of the interconnection lines is carried out by white room technologies known to those skilled in the art.

The method according to the invention makes it possible to manufacture an intraocular retinal implant including both a flexible substrate and electrodes made of doped diamond. The fact that the substrate is flexible makes it possible to obtain an implantation that is not very invasive, as well as a better contact with the tissues by hugging as best as possible the shape of the retina. Obtaining a better contact makes it possible, among other things, to use lower levels of stimulation currents, which ultimately leads to an increase in the geometric resolution of the implant.

The implant produced according to the method of the invention may be implanted on or under the retina for several years without creating any modification of the surrounding tissues (no formation of glial cells or necrosis of the tissues, etc.). The performance of the implant does not degrade over time, thereby avoiding any subsequent intervention aiming to change or to modify the implant.

This implant can make it possible to produce an artificial retina. It is adapted to an implantation in living retinal tissues to enable, for example, the restoration of sight in certain patients affected by degeneration of their photoreceptors.

It is possible to produce planar implants in which the distal ends of the electrodes are substantially at the same level as the surface of the flexible plate on which they are located; it is also possible to produce implants in which the electrodes have a three-dimensional structure and are projecting from the flexible plate on which they are arranged, which allows them to reach more easily the areas of specific interest in the retinal tissue and to ensure an anchoring in the tissues, thereby avoiding a movement of the implant by sliding on the cellular tissues of the retina. The three-dimensional structures of the electrodes may be any elongated shape, such as for example a cylindrical, pyramidal, conic, parallelepiped shape, etc.

BRIEF DESCRIPTION OF DRAWINGS

The invention will be better understood and other advantages and particularities will become clear on reading the description that follows, given by way of non-limiting example, accompanied by the appended drawings among which.

DETAILED DESCRIPTION OF PARTICULAR EMBODIMENTS

The method according to the invention makes it possible to produce an intraocular retinal implant formed of a set of electrodes made of doped diamond arranged on a flexible substrate.

The electrodes are preferably microelectrodes, in other words electrodes in which the largest dimension is comprised between 1 and 1000 micrometers, preferably between 1 and 100 micrometers.

In the case where the electrodes have an elongated shape, for example a column shape, it will then have a diameter less than the largest dimension, in this particular instance the height; the diameter will thus also be of micrometric value or less.

As first embodiment example, the manufacture of a planar implant with electrodes made of diamond doped with boron will be described.

In order to obtain a localised growth of the doped diamond on the substrate, the mould is produced by using the structuring method disclosed in the document [4], which consists in structuring a layer of diamond particles deposited on the face of a substrate. To obtain the structuring of the layer of diamond, any of the techniques disclosed in this document [4] may be used.

For example, to produce a mould 100 on the upper face of a silicon substrate 1, a sacrificial layer 2 is deposited, for example a silicon oxide layer having a thickness of 1.5 µm. Said sacrificial layer will aid the removal of the substrate at the end of the method for manufacturing the implant. It is however pointed out that said sacrificial layer 2 is not essential and can quite easily be omitted.

Figure 1A:
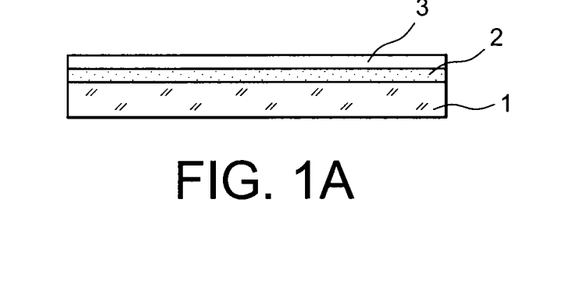
FIGS. 1A to 1K represent the steps of the method of the invention according to a first variant making it possible to obtain a planar implant.

Then, a layer of diamond particles 3 is deposited on the sacrificial layer 2 (FIG. 1A) so as to obtain a density of diamond particles of around $10^{10}$ to $10^{11}$ particles per $cm^2$. The diamond particles may for example be particles of the nano-powder SYNDIA® supplied by the company Van Moppes, in Switzerland, having the reference 11247; said powder has the following characteristics: 14.8 carats/kg and a "0-0.02 GAF" grade, in other words that the diamond powder is conditioned in the form of liquid diamond (it is in solution and not in dry form) and is GAF (guaranteed agglomerates free), with particles of sizes comprised between 0 and 0.02 µm.

Figure 1B:
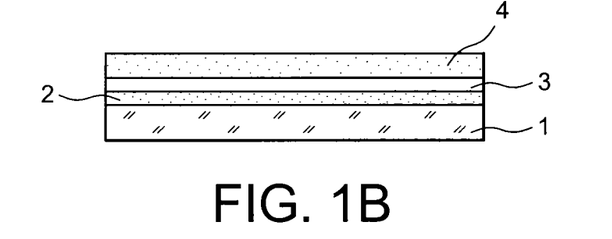

Then, a layer of positive or negative photosensitive resin 4 is deposited on the layer of nano-diamond powder 3 (FIG. 1B).

Figure 1C:
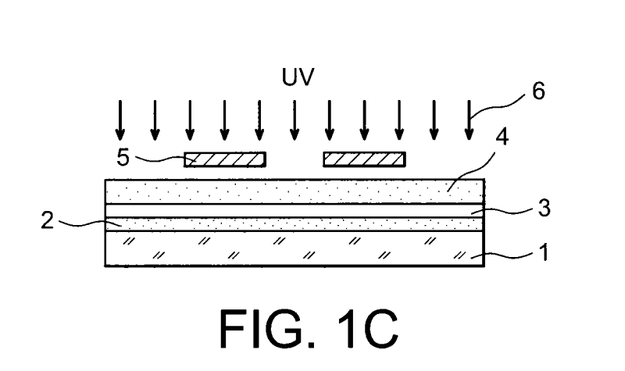

Said layer of photosensitive resin 4 is then insolated in a selective manner by an electromagnetic radiation 6 (for example Ultra-Violet (UV) rays) through a mask 5 (FIG. 1C), the patterns of which are selected as a function of the microstructuring patterns that it is wished to give to the future layer of diamond.

Figure 1D:
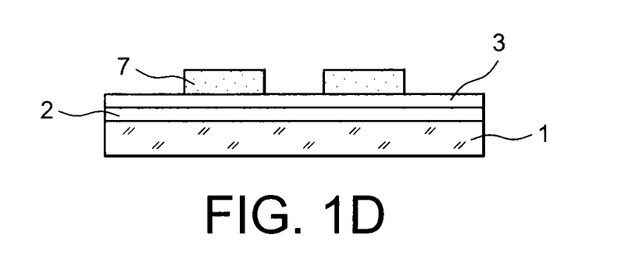

The layer of photosensitive resin 4 is then developed according to a known technique, in order to obtain a layer of microstructured photosensitive resin 7 on the substrate (FIG. 1D).

Figure 1E:
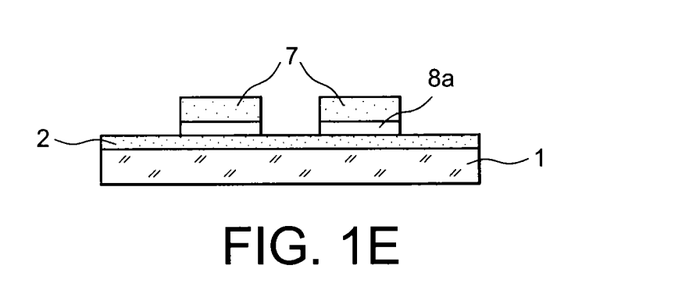

The following step consists in lifting off the areas of the layer of nano-diamond powder 3 that are not covered (masked) by the layer of microstructured resin 7, to end up with a layer of structured nano-diamond powder 8a. To do this, the substrate provided with its different layers is for example placed in a plasma environment containing a gas or a mixture of gases to carry out the etching of the layer of nano-diamond powder 3 (FIG. 1E). The gas used for the etching may be for example $SF_6$, or instead a suitable mixture of oxygen and argon.

Figure 1F:
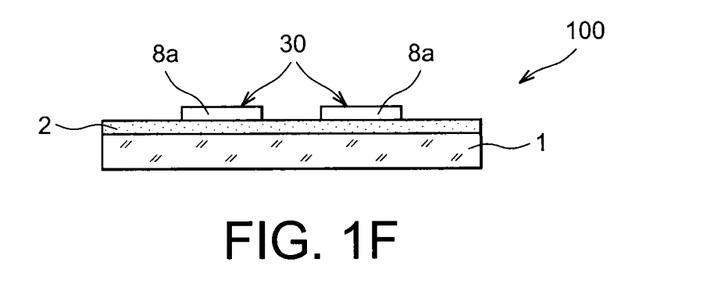

The layer of microstructured resin 7 is then lifted off with a suitable liquid solution, for example with concentrated nitric acid: a mould 100 is then obtained comprising a substrate 1, one face of which is provided with a layer of structured nano-diamond powder 8a (FIG. 1F).

Figure 1G:
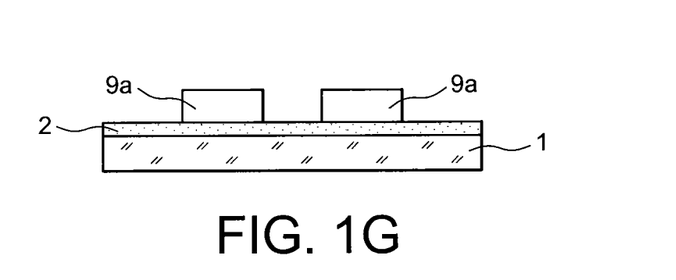

Finally, a layer of microstructured diamond 9a is made to grow on the microstructured layer of diamond nano-powder (FIG. 1G).

In this embodiment, it may be noted that it is the elements in relief 30 on the mould that are going to form the electrodes of doped diamond during the transformation of the nano-diamond powder into doped diamond material (transformation of the elements 8a into the elements 9a).

Several methods exist to synthesise a layer of diamond. The most widely used methods are chemical deposition methods from a plasma enhanced vapour phase (or PECVD, for Plasma Enhanced Chemical Vapour Deposition) type growth method, the plasma being able to be in the micro-wave (MPCVD) or radio-frequency (RFCVD) range or chemical deposition methods from a hot filament enhanced vapour phase.

In our embodiment, it is possible for example to place the device in a MPCVD type growth reactor. The MPCVD method consists in making diamond grains of nanometric size grow on a substrate placed in a MPCVD growth reactor at 2.45 GHz, typically operating between 0.5 and 6 kilowatts, supplied with a gaseous mixture including at least a mixture of methane and hydrogen in suitable proportion (in other words, a proportion of methane comprised between 0.1 and 5%). In our example, the conditions for growing the doped diamond are the following:

- a microwave power of 1000 watts;
- a mixture of gases includes 99% of hydrogen, 1% of methane and 100 ppm of trimethyl boron, the mixture being at a pressure of 50 mBars;
- the substrate is heated to a temperature of 700° C.

After 20 hours, the growth of the electrodes of diamond doped with boron is stopped.

Figure 1H:
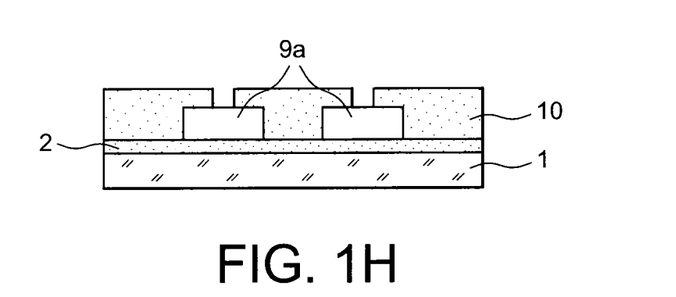

Then, a first deposit of a layer of polyimide 10 is carried out on the upper face of the substrate 1 covering the electrodes 9a. The deposition may be carried out by spin coating. The polyimide may, for example, be the reference PI 2611 from Dupont.

The layer of polyimide 10 then undergoes an annealing at 350° C. under nitrogen.

Said layer of polyimide 10 leaves exposed the electrodes 9a (FIG. 1H). To do this, the layer of polyimide 10 may for example be photolithographed: a layer of any material that can serve as mask is deposited on the whole of the upper face of the substrate (for example, it is possible to deposit on a layer of metal such as aluminium by PVD (Plasma Vapour Deposition), then a step of photolithography is used in order to define the shape of the implant (its contours) and to establish the contacts on the micro-electrodes by forming interconnection lines.

Once the layer of aluminium has been etched, for example by plasma of a $Cl_2/BCl_3/Ar$ mixture, the polyimide is in its turn etched by plasma in an $O_2/Ar$ mixture.

The layer of aluminium serving as masking is then removed in an orthophosphoric acid bath at 60° C.

Finally, interconnection lines 11 are formed (FIG. 1I); said lines are going to make it possible to connect the electrodes 9a to the electronic system (not represented) that is going to supply the electrical energy. To do this, a deposition of titanium and gold is carried out on the layer of polyimide and on the electrodes made of doped diamond. Said interconnection lines 11 may be obtained by a step of photolithography.

Figure 1I:
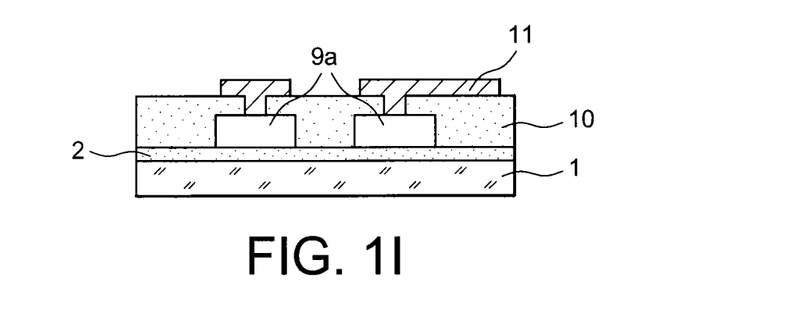

A second polyimide layer 12 is produced as previously. It here involves with said second layer 12 electrically insulating all the interconnection lines 11 from the external environment.

Figure 1J:
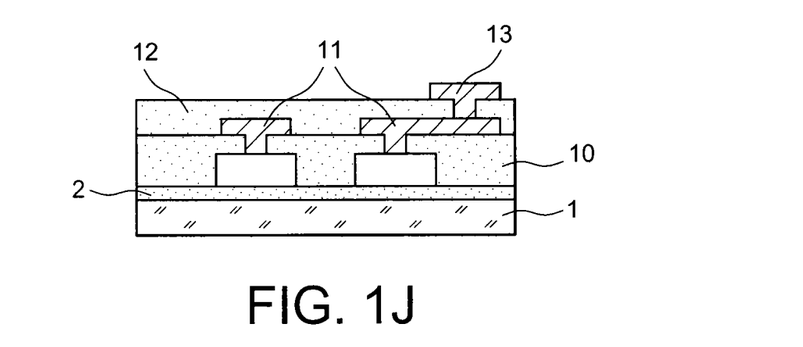

On the second polyimide layer 12 is deposited a layer of aluminium that is going to serve as etching mask, then said layer of polyimide is etched, for example by $Ar/O_2$ plasma, at certain locations until certain interconnection lines are reached in order to form contact pads 13 that will serve to connect the electrodes to the electronic system delivering the electrical stimulations.

The layer of aluminium is then dissolved as previously in an orthophosphoric acid bath (FIG. 1J).

Figure 1K:
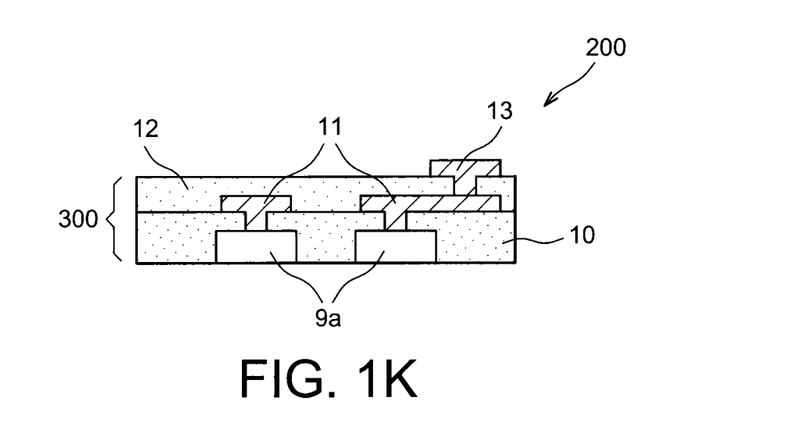

The implant 200 is then disbonded from the mould 100 by placing the substrate 1 in a bath of hydrofluoric acid that is going to etch the sacrificial layer 2 of silicon oxide (FIG. 1K). The implant obtained indeed includes a flexible plate 300 (formed of the first 10 and the second 12 electrically insulating layer) one face of which comprises electrodes 9a made of doped diamond.

The implant once disbonded is then rinsed and dried; it will be sterilised before being implanted in the patient.

It should be noted that it is entirely possible to produce several implants at the same time on a same substrate.

Figure 2A:
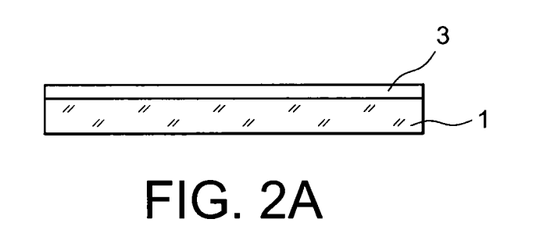
FIGS. 2A to 2I represent the steps of the method of the invention according to a second variant making it possible to obtain a planar implant.

Other embodiment variants are possible. For example, another technique disclosed in the document [4] consists in depositing, on the upper face of a silicon substrate 1, a layer of diamond particles 3 (FIG. 2A) so as to obtain, as in the preceding example, a density of diamond particles of around $10^{10}$ to $10^{11}$ particles per $cm^2$. It is pointed out that in this example, no sacrificial layer has been deposited between the substrate and the layer of nano-diamond powder, but it is entirely possible to do this, as in the preceding example.

Figure 2B:
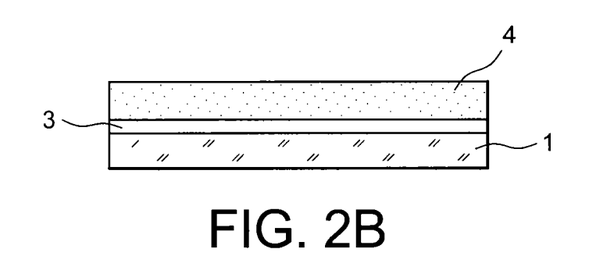

Then, a layer of positive or negative photosensitive resin 4 is deposited on the layer of nano-diamond powder 3 (FIG. 2B).

Figure 2C:
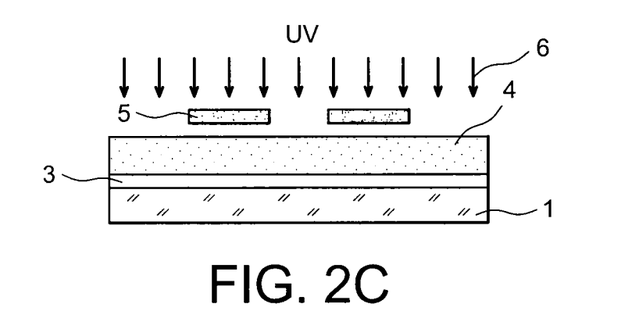

Said layer of photosensitive resin 4 is then insolated in a selective manner with an electromagnetic radiation 6 through a mask 5 (FIG. 2C).

Figure 2D:
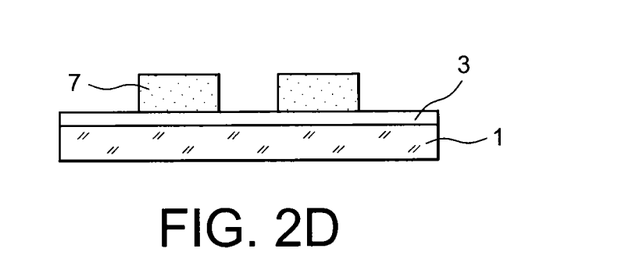

The layer of photosensitive resin 4 is then developed according to a known technique, in order to obtain a microstructured layer of photosensitive resin 7 on the substrate (FIG. 2D).

Figure 2E:
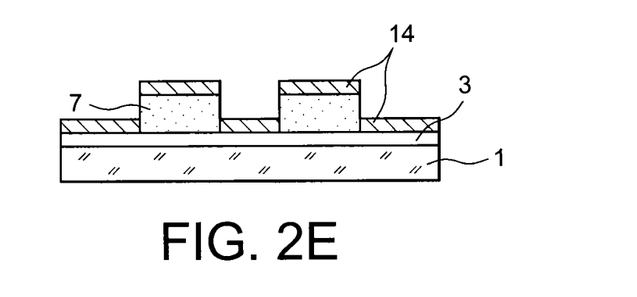
Figure 2F:
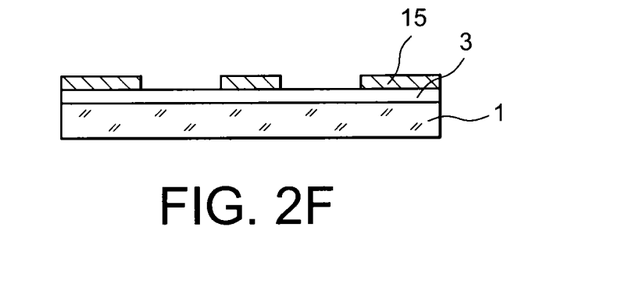

The following step consists in depositing a metal layer 14 (for example a layer of aluminium) on the surface (FIG. 2E), then lifting off the resin as well as the parts of the metal layer situated below the layer of resin. By lift-off method, a microstructured metal layer 15 (FIG. 2F) is thereby obtained.

Figure 2G:
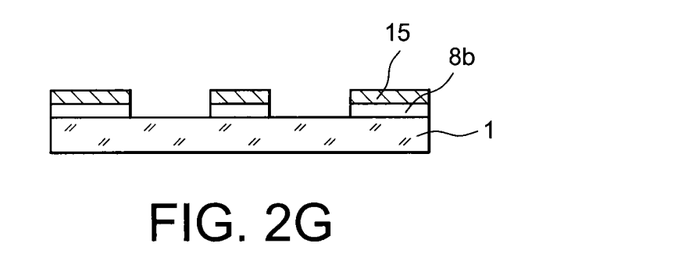

Then, the areas of the layer of nano-diamond powder 3 which are not covered (masked) by the microstructured metal layer 15 are lifted off, to end up with a structured layer of nano-diamond powder 8b below the metal layer (FIG. 2G).

Figure 2H:
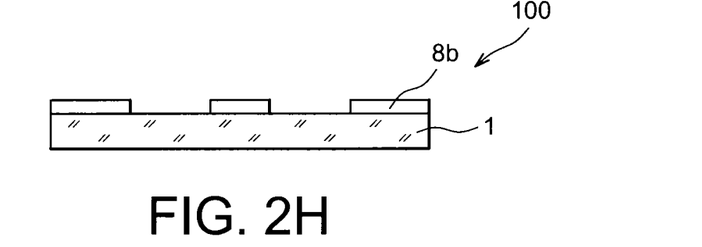

The structured metal layer 15 is then lifted off with a suitable liquid solution, for example a caustic soda solution of 5M concentration: a mould 100 is then obtained comprising a substrate 1, one face of which is provided with a structured layer of nano-diamond powder 8b (FIG. 2H).

Figure 2I:
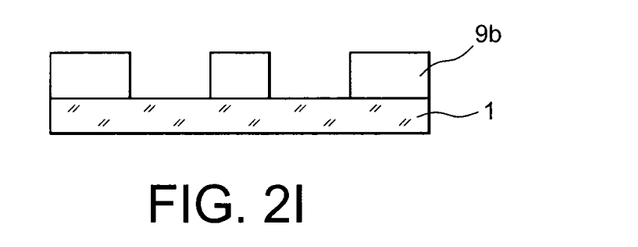

Finally, a layer of microstructured diamond 9b is made to grow on the microstructured layer of diamond nano-powder 8b (FIG. 2I).

In this embodiment, it is also the elements in relief on the mould that are going to form the electrodes of doped diamond during the transformation of the nano-diamond powder into doped diamond material (transformation of the elements 8b into the elements 9b).

The production of the implant is continued by carrying out steps similar to those presented in the preceding example (FIGS. 1H-1K) to produce the layers of electrically insulating material and the interconnection lines.

As a final embodiment example, the manufacture of a three-dimensional implant in which the electrodes made of doped diamond are projecting with respect to the surface of the flexible plate of the implant will be described.

Figure 3A:
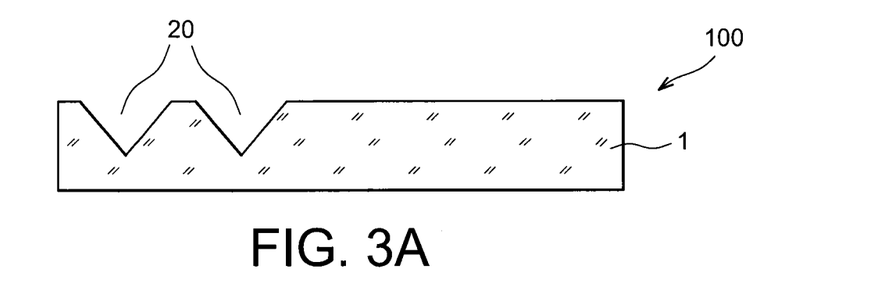
FIGS. 3A to 3G represent the steps of the method according to the invention according to a third variant making it possible to produce an implant comprising three-dimensional electrodes.

The manufacturing method is similar to that described for the first example. Only the preparation of the mould 100 is different. In fact, before carrying out the steps described in the first example, cavities 20 are formed in the substrate 1 (FIG. 3A). Here, unlike the preceding example, it may be noted that it is the depressed elements of the mould (the cavities 20) that are going to form the electrodes of doped diamond: said cavities form the pattern cavity for the electrodes that it is sought to obtain.

A substrate 1 of oriented silicon (100), having preferably a thickness greater than 300 micrometers, is oxidised so as to obtain a silicon oxide layer of around 400 nm thickness on the upper face, said layer serving as etching mask.

The silicon oxide layer is etched locally using a technique of photolithography to demarcate the location of the future electrodes.

Then the substrate is placed in a KOH bath at 80° C.

As a function of the pattern of the etching mask and the crystallographic orientation of the substrate, cavities of different shapes may be obtained. For example, when openings of square shape are formed in the oxide layer, the anisotropic etching of the silicon substrate in the bath of KOH will give pyramidal cavities. In the same way, by varying the etching time, more or less deep cavities are obtained.

Typically, the height of the three-dimensional electrodes will be comprised between 1 and 100 micrometers; the depth of the cavities will thus be comprised within said same values.

Once the cavities are formed, the substrate is cleaned.

Figure 3B:
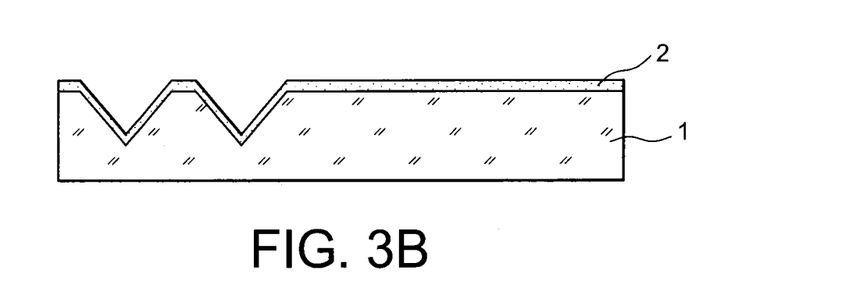

Then, a thick layer of silicon oxide, for example a layer of 1.5 μm thickness, is deposited on the upper face of the substrate: it will serve as sacrificial layer 2. It is pointed out that the addition of said sacrificial layer is optional (FIG. 3B).

Then, the same steps as those described in the first example are used to terminate the three-dimensional implant.

A layer of diamond particles is thus deposited in the places where it is wished to obtain the diamond electrodes, namely on the walls of the cavities of the mould—a "nanoseeding" is carried out—then, the growth of the diamond layer 9a (FIG. 3C) is carried out. It should be noted that it is possible to form a layer of diamond uniquely on the walls of the cavities or, quite the opposite, in all the space occupied by the cavities. In this latter case, the growth of the diamond is stopped when the whole of the space of the cavities of the mould will be filled with doped diamond.

Figure 3C:
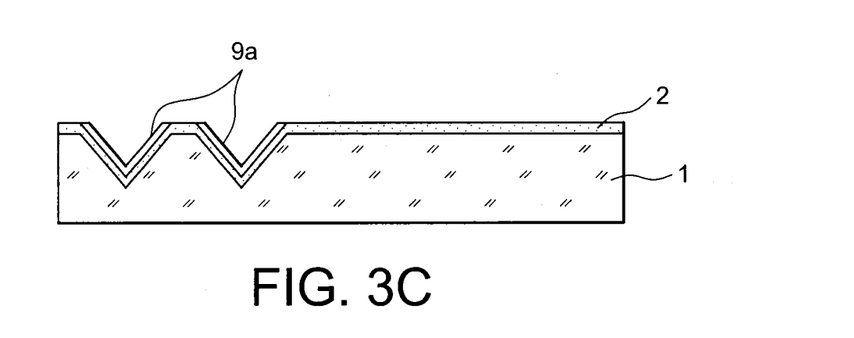

Then, a layer of electrically insulating and biocompatible material 10 (for example a polymer) is deposited on the face of the mould comprising the electrodes in order to cover all of the three-dimensional structure of the face of the mould, including the electrodes 9a.

Figure 3D:
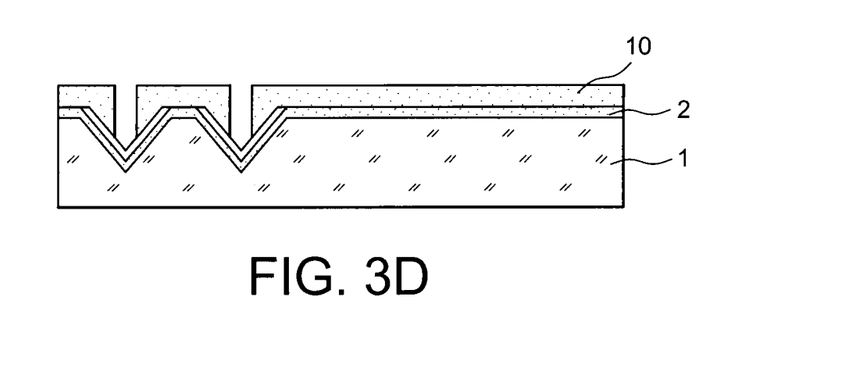

A local etching is then carried out in order to open contacts on the electrodes 9a (FIG. 3D).

Figure 3E:
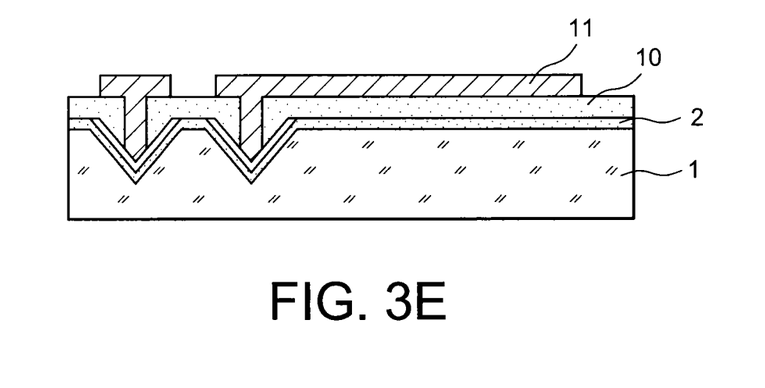

The interconnection lines 11 are then formed by standard deposition (PDV or evaporation) of an electrically conductive material, for example a metal, and by photolithographies (FIG. 3E).

Figure 3F:
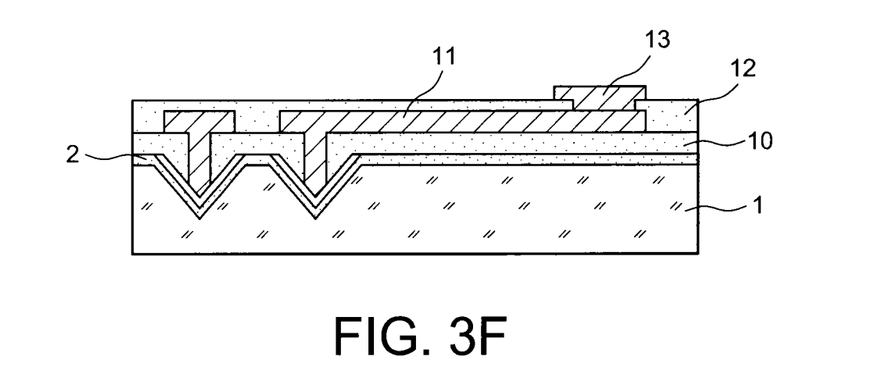

A second layer 12 of electrically insulating and biocompatible material, for example a polymer and, preferably, the same material used for the first layer, is deposited on the structure and etched to define the shape of the implant (FIG. 3F).

Contacts 13 may be formed that will make it possible to connect the interconnection lines 11 to a current source. The openings for the formation of said contacts may be formed during the etching of the first layer of electrically insulating material or during the etching of the second layer of electrically insulating material, in other words during step 3D or 3F.

Figure 3G:
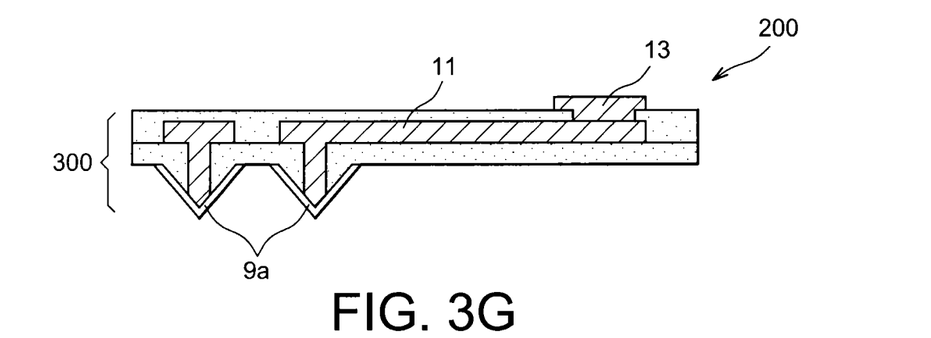

Finally, the sacrificial layer 2 is etched by chemical process, which has the effect of detaching the implant 200 from the mould 100 (FIG. 3G).

BIBLIOGRAPHY

[1] WO 2007/148038 A1.
[2] K. Hungar et al., "Production processes for a flexible retina implant", Sensors and Actuators A, Physical, 123-124, 2005, pg 172-178.
[3] P. Bergonzo, "Des diamonds pour la vue", CEA Techno, N°89, June 2008, pg 6.
[4] FR 08 55128

The invention claimed is:

1. A method for manufacturing an intraocular retinal implant, that can stimulate cells of a retina by sending electrical impulses to produce an artificial vision, the implant including a flexible plate made of a biocompatible and electrically insulating material, which includes, on one face thereof, a plurality of electrodes made of doped diamond spaced apart from each other and connected to interconnection lines configured to lead an electric current to the electrodes so that they can transmit electrical impulses to cells of the retina, the method comprising:
   a) providing a mold capable of supporting growth of a layer of doped diamond, the mold comprising, on one face thereof, a set of elements, which are all depressed or all projecting with respect to the surface of the face, and which constitute a pattern cavity for the electrodes of the implant which it is desired to obtain;
   b) producing electrodes made of doped diamond by growing a layer of doped diamond in all or part of a space occupied by the elements of the pattern cavity;
   c) forming a first layer of electrically insulating material on the face of the mold comprising the pattern cavity, the first layer covering at least a space between the electrodes, while leaving uncovered at least a part of the surface of each electrode;
   d) producing interconnection lines by depositing an electrically conductive material at least in spaces not covered by the first layer of electrically insulating material;
   e) forming a second layer of electrically insulating material on the face of the mold including the pattern cavity, the second layer covering the interconnection lines and the first and the second layers of electrically insulating material forming the flexible plate of the implant; and
   f) removing the mold, thus obtaining the intraocular retinal implant.

2. A method according to claim 1, wherein the materials of the first and the second layers are a same material.

3. A method according to claim 1, wherein the removing f) is obtained by chemical or mechanical elimination of the mold.

4. A method according to claim 1, further comprising, between the providing a) and the producing b) depositing, on the face of the mold comprising the pattern cavity, a sacrificial layer supporting the growth of a layer of doped diamond, the sacrificial layer being configured to be lifted off during the removing f).

5. A method according to claim 4, wherein the removing f) is obtained by dissolution of the sacrificial layer or by detaching the sacrificial layer.

6. A method according to claim 1, wherein a greatest extent of the electrodes measured in a direction parallel to the plane of the face of the flexible plate comprising the electrodes is of micrometric dimension or less.

7. A method according to claim 1, wherein a distance that separates two adjacent electrodes is of micrometric dimension or less.

8. A method according to claim 1, wherein the doped diamond is diamond doped with boron.

9. A method according to claim 1, wherein the providing a) includes:
   providing a substrate capable of supporting the growth of a layer of doped diamond on one of faces thereof;
   depositing a layer of diamond powder on the face of the substrate, grains of the diamond powder having a nanometric size;
   depositing a layer of photosensitive resin of a determined thickness on the layer of diamond powder;

structuring the layer of diamond powder by photolithography of the layer of photosensitive resin to obtain the pattern cavity of the mold.

10. A method according to claim 1, wherein the producing a) includes:
- providing a substrate capable of supporting growth of a layer of doped diamond on one of the faces thereof;
- depositing a layer of diamond powder on the face of the substrate, grains of the diamond powder having a nanometric size;
- depositing a layer of photosensitive resin of a determined thickness on the layer of diamond powder;
- structuring the layer of photosensitive resin by photolithography until the layer of diamond powder is reached;
- depositing a metal layer on the face of the substrate, the metal layer covering the structured resin layer and the layer of diamond powder not masked by the structured resin layer;
- removing the structured resin layer so as to form a structured metal layer;
- structuring the layer of diamond powder by etching the layer of diamond powder not masked by the structured metal layer;
- removing the structured metal layer to obtain the pattern cavity of the mold.

* * * * *